(12) United States Patent
Gill et al.

(10) Patent No.: US 8,571,642 B2
(45) Date of Patent: Oct. 29, 2013

(54) PRE-EJECTION INTERVAL (PEI) MONITORING DEVICES, SYSTEMS AND METHODS

(75) Inventors: Jong Gill, Valencia, CA (US); Brian Jeffrey Wenzel, San Jose, CA (US); Allen Keel, San Francisco, CA (US); Wenbo Hou, Lancaster, CA (US); Edward Karst, South Pasadena, CA (US); Taraneh G. Farazi, Santa Clara, CA (US)

(73) Assignee: Pacesetter, Inc., Sylmar, CA (US)

( * ) Notice: Subject to any disclaimer, the term of this patent is extended or adjusted under 35 U.S.C. 154(b) by 427 days.

(21) Appl. No.: 12/882,084

(22) Filed: Sep. 14, 2010

(65) Prior Publication Data

US 2012/0065528 A1    Mar. 15, 2012

(51) Int. Cl.
*A61B 5/02* (2006.01)
(52) U.S. Cl.
USPC .......................................... 600/513; 600/500
(58) Field of Classification Search
None
See application file for complete search history.

(56) References Cited

U.S. PATENT DOCUMENTS

| | | |
|---|---|---|
| 4,719,921 A | 1/1988 | Chirife |
| 4,773,401 A * | 9/1988 | Citak et al. ............... 607/17 |
| 4,865,036 A | 9/1989 | Chirife |
| 5,154,171 A | 10/1992 | Chirife |
| 5,168,869 A | 12/1992 | Chirife |
| 5,549,650 A * | 8/1996 | Bornzin et al. ............... 607/24 |
| 8,428,699 B2 * | 4/2013 | Pinter et al. ............... 600/509 |
| 2006/0094967 A1 * | 5/2006 | Bennett et al. ............... 600/508 |
| 2007/0293770 A1 * | 12/2007 | Bour et al. ............... 600/481 |
| 2008/0027341 A1 * | 1/2008 | Sackner et al. ............... 600/509 |
| 2009/0030292 A1 * | 1/2009 | Bartnik et al. ............... 600/301 |
| 2010/0312115 A1 * | 12/2010 | Dentinger ............... 600/450 |
| 2011/0066041 A1 * | 3/2011 | Pandia et al. ............... 600/484 |
| 2011/0224555 A1 * | 9/2011 | Park ............... 600/483 |
| 2011/0319724 A1 * | 12/2011 | Cox ............... 600/301 |

OTHER PUBLICATIONS

Cvetkovic et al., Wavelet transform feature extraction from human PPG,ECG, and EEG signal responses to EIF PEMF exposures: A pilot study, Jun. 2007.

* cited by examiner

*Primary Examiner* — Kennedy Schaetzle

(57) ABSTRACT

Provided herein are implantable systems, and methods for use therewith, for monitoring a patient's pre-ejection interval (PEI). A signal indicative of cardiac electrical activity and a signal indicative of changes in arterial blood volume are obtained. One or more predetermined features of the signal indicative of cardiac electrical activity and the signal indicative of changes in arterial blood volume are detected. The patient's PEI is determined by determining an interval between the predetermined feature of the signal indicative of cardiac electrical activity and the predetermined feature of the signal indicative of changes in arterial blood volume.

20 Claims, 10 Drawing Sheets

PRE-EJECTION INTERVAL (PEI) MONITORING DEVICES, SYSTEMS AND METHODS

FIELD OF THE INVENTION

Embodiments of the present invention relate to devices, systems and methods for monitoring cardiac pre-ejection interval.

BACKGROUND OF THE INVENTION

A person's circulatory system includes both systemic and pulmonary circulation. Pulmonary circulation supplies the lungs with blood flow, while the systemic circulation takes care of all the other parts of the body. The heart serves as a pump that circulates the blood, while blood vessels act as the conduits that deliver blood to tissue. During systole, that is, during ventricular contraction, blood pressure in the aorta and pulmonary artery rises until their valves close after which the pressure pulse declines to a rather steady state during diastole. A cardiac cycle begins with initiation of the QRS complex in the electrocardiogram or intracardiac electrogram (ECG or IEGM) waveform. It takes a certain amount of time for a heart stimulus signal to propagate and to effect depolarization of the ventricular tissue cells so there is a short delay before ventricular contraction starts. The time elapsed between the beginning of the QRS complex and the onset of ventricular contraction can be defined as the pre-ejection interval (PEI).

PEI has been shown to be an important parameter to assess cardiac functionality. For example, an increase in PEI indicates worsened heart failure condition while a shorter PEI indicates an improved heart failure condition. One approach used to obtain a measurement of PEI involves using Echo measurements. However, such an approach typically is costly and time-consuming. Additionally, obtaining a measurement of PEI using Echo-based measurements makes it difficult to measure PEIs continuously.

Accordingly, it would be beneficial to provide less costly and time consuming measures of for monitoring PEI.

SUMMARY

Certain embodiments of the present invention relate to implantable systems and methods for use therewith, for monitoring a patient's pre-ejection interval (PEI).

In an embodiment, one or more electrodes implanted within and/or on the patient's heart are used to obtain a signal indicative of cardiac electrical activity. In an embodiment, the electrode(s) is/are used to obtain an intracardiac electrogram (IEGM) signal indicative of cardiac electrical activity. In an alternative embodiment, the electrode(s) is/are used to obtain an electrocardiogram (ECG) signal indicative of cardiac electrical activity. Additionally, an implanted sensor is used to obtain a signal indicative of changes in arterial blood volume. In an embodiment, an implanted photoplethysmography (PPG) sensor is used to obtain a PPG signal indicative of changes in arterial blood volume. In an alternative embodiment, an impedance plethysmography (IPG) sensor is used to obtain an IPG signal indicative of changes in arterial blood volume. Other sensors can alternatively be used to obtain other signals indicative of changes in arterial blood volume.

In certain embodiments, a predetermined feature of the IEGM or ECG signals indicative of cardiac electrical activity is detected. The predetermined feature of the IEGM/ECG signals indicative of cardiac electrical activity is preferable indicative of ventricular depolarization. Exemplary predetermined features indicative of ventricular depolarization include, but are not limited to, a Q-wave, a R-wave and a QRS complex.

In an embodiment, a predetermined feature of the PPG or IPG signals indicative of changes in arterial blood volume is detected. The predetermined feature of the PPG/IPG signals indicative of arterial blood volume is preferably indicative of the systolic portion of the signal. The morphology of PPG/IPG signals is relatively consistent beat to beat around the systolic portion of the signal. This consistency of the morphology around the systolic portion of the PPG/IPG signal can allow for robust and reliable selection of a predetermined feature that can serve as a basis for determining an interval indicative of a patient's PEI. Exemplary predetermined features corresponding to the systolic portion of the PPG/IPG signal indicative of changes in arterial blood volume can be, but are not limited to, a foot, a peak and a maximum positive slope of the signal.

In certain embodiments, a patient's PEI can be monitored by determining an interval between the predetermined feature of the signal indicative of cardiac electrical activity and the predetermined feature of the signal indicative of changes in arterial blood volume. For example, the patient's PEI can be monitored by determining an interval between a predetermined feature indicative of ventricular depolarization of the signal indicative of cardiac electrical activity and a predetermined feature corresponding to a systolic portion of the signal indicative of changes in arterial blood volume. In an embodiment, triggering an alert, and/or therapy and/or adjusting therapy can be based on the monitored PEI.

Additional and alternative embodiments, features and advantages of the invention will appear from the following description in which the preferred embodiments have been set forth in detail, in conjunction with the accompanying drawings and claims.

DETAILED DESCRIPTION OF THE INVENTION

Figure 1A:
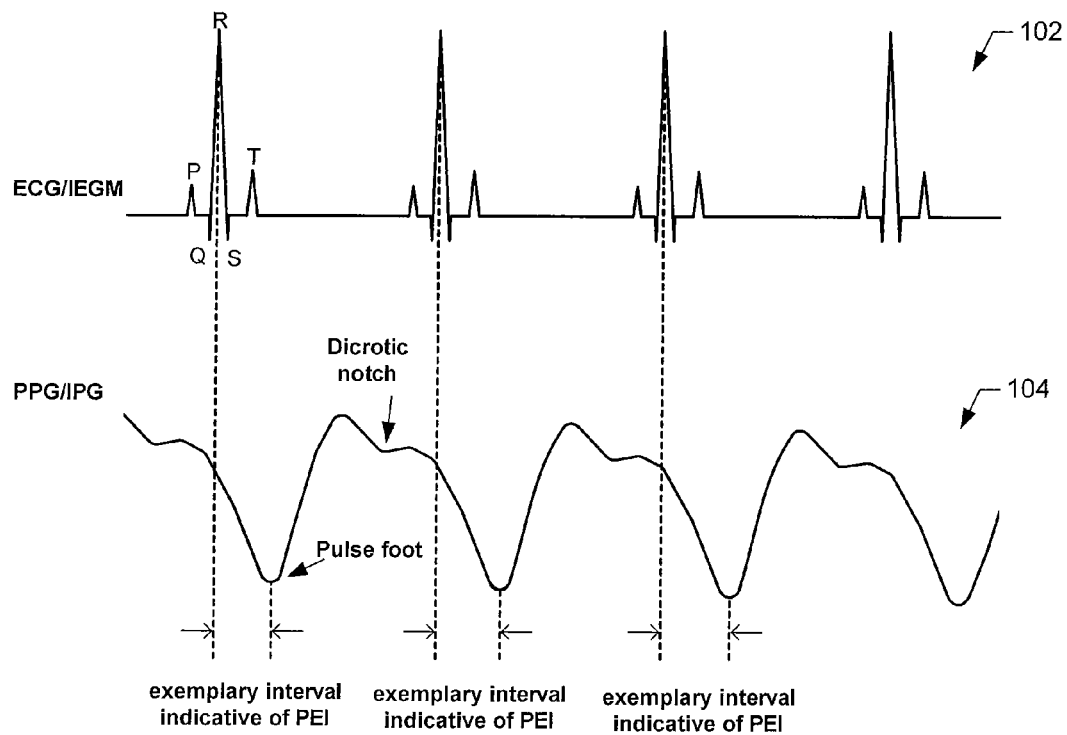
FIG. 1A includes exemplary signal waveforms that are used to show the relative timing of various signals, and how an exemplary interval indicative of pre-ejection interval (PEI) can be determined in accordance with an embodiment of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Referring to FIG. 1A, the representative signal waveforms therein are used to show the relative timing of electrical and mechanical cardiac events that occur during cardiac cycles. The upper most waveform is representative of an electrocardiogram (ECG) or intracardiac electrogram (IEGM) signal 102 (collectively referred to as ECG/IEGM signal 102), which is indicative of electrical activity of the patient's heart. The following waveform is representative of a photoplethysmography (PPG) signal or impedance plethysmography signal (IPG) 104, both of which are indicative of changes in arterial blood volume. Signal 104 is also indicative of mechanical activity of a patient's heart. For example, the PPG or IPG signal 104 (collectively referred to as PPG/IPG signal 104) is indicative of mechanical activity of the patient's heart because the PPG/IPG signal 104 represents changes in the flow of blood through the vessels probed by the PPG/IPG sensor (or stated another way, changes in arterial blood volume), which is dependent on the mechanical activity of the heart.

Referring to the ECG/IEGM signal 102, each cycle of the signal 102 is shown as including a P wave, a QRS complex (including Q, R and S waves) and a T wave. The P wave is caused by depolarization of the atria. This is followed by atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole.

Figure 1B:
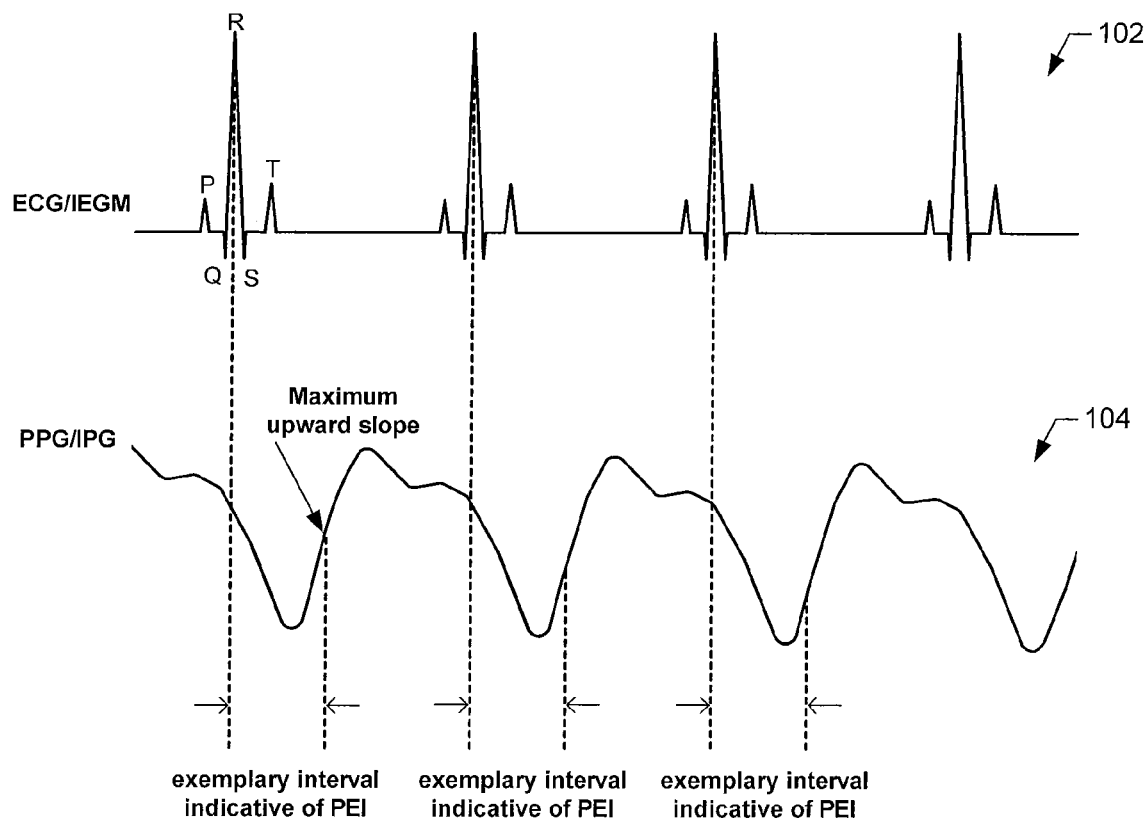
FIG. 1B includes the same exemplary signal waveforms shown in FIG. 1A, but shows how another exemplary interval indicative of PEI can be determined in accordance with an embodiment of the present invention.
Figure 1C:
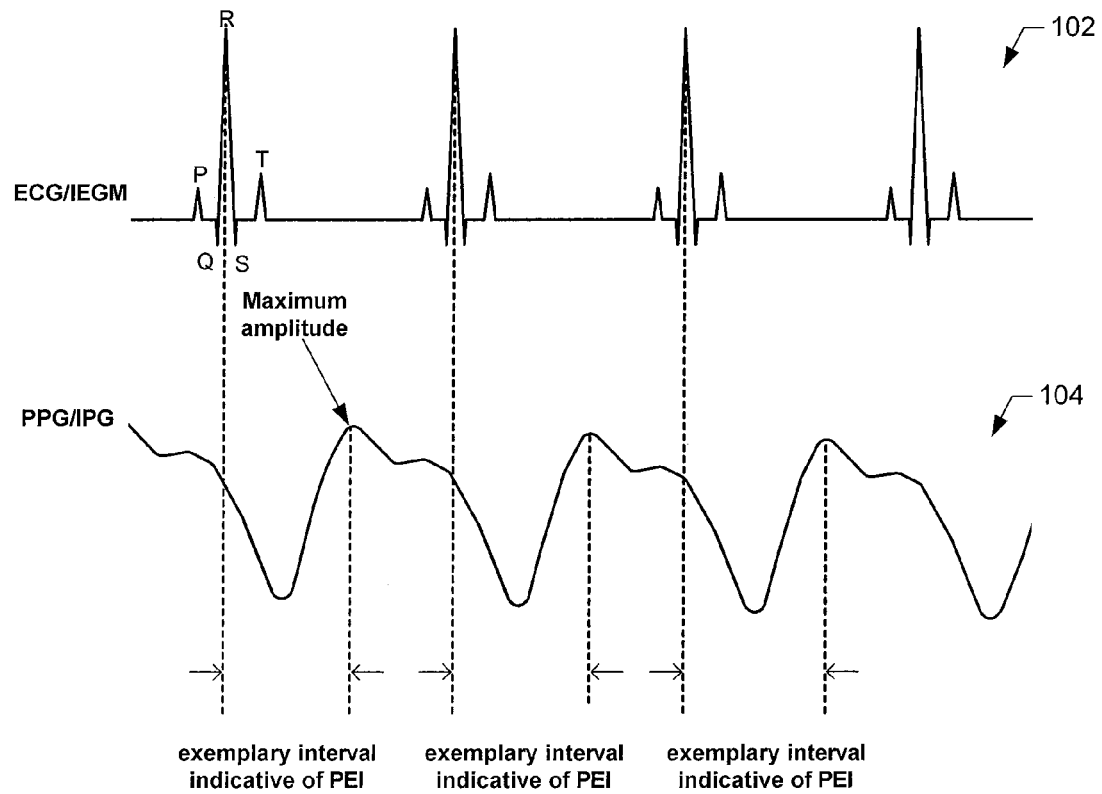
FIG. 1C is similar to FIG. 1A, and shows how still another exemplary interval indicative of PEI can be determined in accordance with an embodiment of the present invention.

An exemplary interval indicative of pre-ejection interval (PEI) is also shown in FIG. 1A. In general, an interval indicative of PEI can be determined, in accordance with embodiments of the present invention, by determining a time from a detected predetermined feature of an ECG/IEGM signal (e.g., 102) to a detected predetermined feature of the signal indicative of changes in arterial volume, which can be a PPG/IPG signal (e.g., 104), but is not limited thereto. The predetermined feature of the signal indicative of cardiac electrical activity is preferable indicative of ventricular depolarization. The predetermined feature of the signal indicative of arterial blood volume is preferably indicative of the systolic portion of the signal. In FIG. 1A, the predetermined feature of the ECG/IEGM signal 102 is the R-wave, and the predetermined feature of the PPG/IPG signal 104 is the pulse foot. In other words, the interval indicative of PEI can be determined by determining a time from the R-wave of the ECG/IEGM signal 102 to the pulse foot of the PPG/IPG signal 104, as illustrated in FIG. 1A. Alternatively, as illustrated in FIG. 1B, the interval indicative of PEI can be determined by determining a time from the R-wave of the ECG/IEGM signal 102 to the maximum upward slope of the PPG/IPG signal 104. As illustrated in FIG. 1C the interval indicative of PEI can be determined by determining a time from a R-wave to a maximum amplitude (or some other predetermined feature, e.g., the dicrotic notch) of the PPG/IPG signal 104.

As described above in FIGS. 1A-1C, the interval indicative of PEI can be determined by determining a time from a detected predetermined feature of an ECG/IEGM signal to a detected predetermined feature of the PPG/IPG signal. In accordance with an embodiment, the predetermined feature of the ECG/IEGM signal and the PPG/IPG signal can alternatively be determined using a wavelet transformation. The wavelet transformation provides a consistent and robust technique to detect the predetermined feature of both the ECG/IEGM and PPG/IPG signal used in determining the interval indicative of PEI.

Figure 2A:
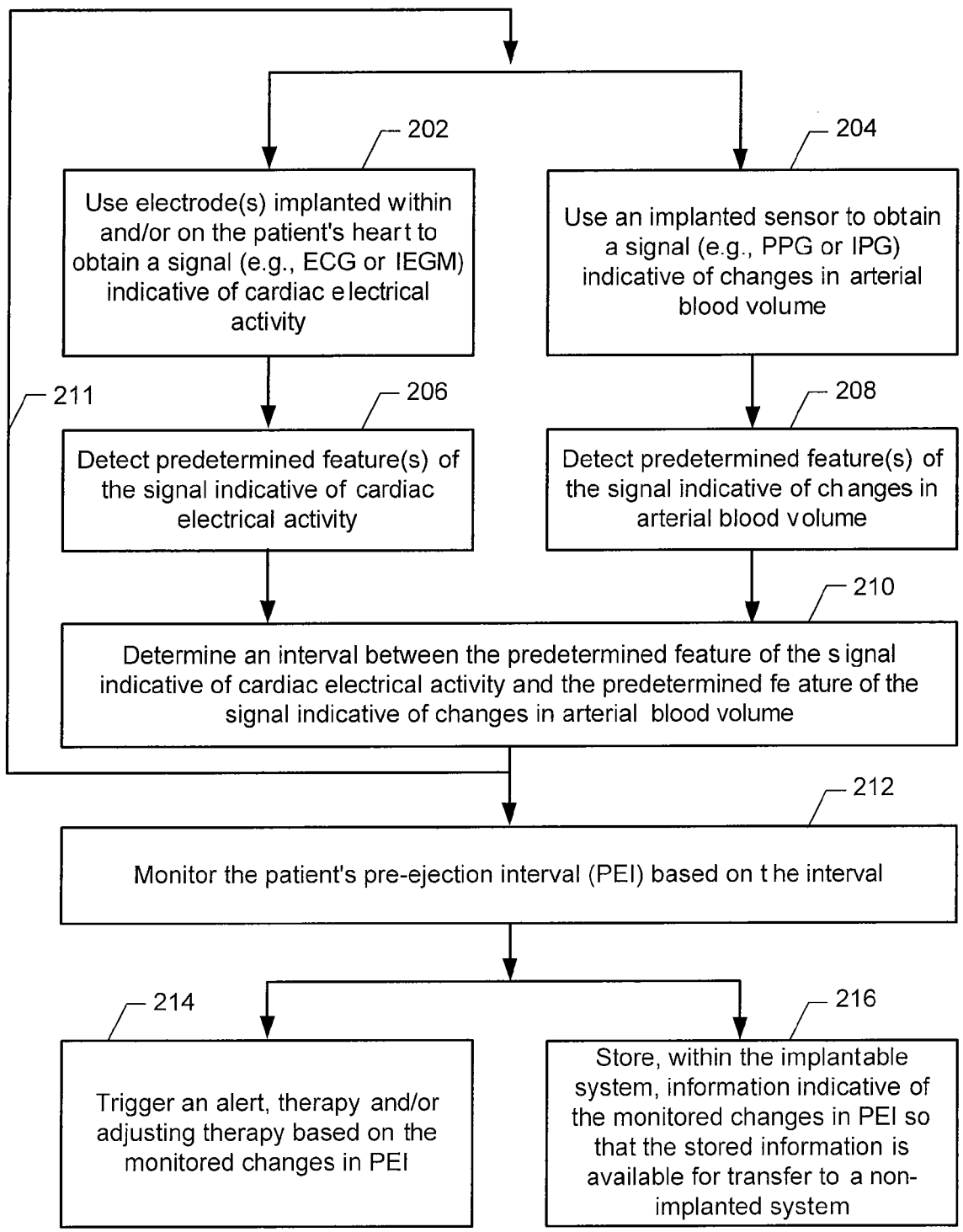
FIG. 2A is a high level flow diagram that is used to explain various embodiments of the present invention that can be used to determine an interval indicative of PEI.

The high level flow diagram of FIG. 2A will now be used to explain various embodiments of the present invention that can be used to determine an interval indicative of PEI. Such embodiments can be implemented by an implantable system, examples of which are discussed below with reference to FIGS. 3 and 4. In FIG. 2A and the other flow diagrams described herein, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 2A, at steps 202 and 204, one or more electrodes implanted within and/or on the patient's heart is/are used to obtain a ECG or IEGM signal indicative of cardiac activity, and an implanted sensor (e.g., optical sensor) is used to obtain a signal indicative of changes in arterial blood volume. The signal indicative of changes in arterial blood volume obtained at step 204 can be a PPG signal, an IPG signal, or some other plethysmography signal. An optical sensor can be used to obtain a PPG signal, or implanted electrodes can be used to obtain an IPG signal. Examples of electrodes and circuitry that can be used to obtain an ECG or IEGM signal are discussed below with reference to FIGS. 3 and 4. Exemplary sensors that can be used to obtain a PPG signal are discussed below with reference to FIGS. 3 and 4. Exemplary sensors (which can include electrodes and circuitry) that can be used to obtain an IPG signal are also discussed below.

In still other embodiments, the plethysmography signal indicative of changes in arterial blood volume can be a signal output by a sensor including a piezo-electric diaphragm. Alternative sensors that can be used to produce the plethysmography signal indicative of changes in arterial blood volume, include, but are not limited to, a close range microphone, a sensor including a small mass on the end of a piezo bending beam with the mass located on the surface of a small artery, a transmission mode infrared motion sensor sensing across the surface of a small artery, or a MEMS accelerometer located on the surface of a small artery. Such alternative sensors can be located, e.g., on the tip of a short lead connected to a device that is subcutaneously implanted. The implanted sensor is preferably close to the patient's aorta. For example, it is preferred that the implanted sensor (used to obtain the signal indicative of changes in arterial blood volume) is 10 mm from the patient's aortic root. Such a sensor can be implanted, e.g., in the pectoral region of a patient. An alternative location for implantation of the sensor includes, but is not limited to, the patient's abdominal region. For the remainder of this discussion, it will be assumed that the signal obtained at step 204 is a PPG or IPG signal, which are collectively referred to as a PPG/IPG signal. However, as just explained above, alternative plethysmography signals can be used.

Still referring to FIG. 2A, at steps 206 and 208, one or more predetermined features of the signal indicative of cardiac electrical activity (e.g., ECG/IEGM) is/are detected, and one or more predetermined features of the signal indicative of changes in arterial blood volume (e.g., the PPG/IPG signal) is/are detected. The one or more predetermined features of the ECG/IEGM signal, detected at step 206, can include features indicative of ventricular depolarization, such as a Q-wave of the ECG/IEGM signal, a R-wave of the ECG/IEGM signal, and/or a QRS complex of the ECG/IEGM signal, but is not limited thereto. At step 208, the predetermined one or more features of the PPG/IPG signal can correspond to a systolic portion of the signal. The morphology of the PPG/IPG signal is relatively consistent beat to beat, especially around the systolic portion of the signal. This consistency of the morphology around the systolic portion of the signal can allow for robust and reliable selection of a predetermined feature that can serve as a basis for determining an interval indicative of a patient's PEI. In accordance with an embodiment, the one or more predetermined features of the PPG/IPG signal can include the pulse foot of the PPG/IPG signal, the pulse peak of the PPG/IPG signal, and/or the maximum positive slope of the PPG/IPG signal, but is not limited thereto. For example, in accordance with an embodiment, a wavelet transformation can alternatively be used to detect a predetermined feature of the ECG/IEGM and PPG/IPG signal used in determining the interval indicative of PEI. Wavelet transformation techniques are well known, and thus need, not be described herein.

At step 210, one or more intervals indicative of PEI is/are determined, where each interval indicative of PEI is determined by determining a time from one of the predetermined features of the signal indicative of cardiac electrical activity (e.g., ECG/IEGM signal) to one of the predetermined features of the signal (e.g., PPG/IPG signal) indicative of changes in arterial blood volume. In accordance with specific embodiments of the present invention, the interval can be determined between a predetermined feature indicative of ventricular depolarization of the signal indicative of cardiac electrical activity and a predetermined feature corresponding to a systolic portion of the signal indicative of changes in arterial blood volume.

As indicated by line 211, steps 202, 204, 206, 208 and 210 can be repeated from time to time (e.g., periodically, aperiodically, in response to a triggering event, etc.), with one or more intervals indicative of the patient's PEI determined each time. Exemplary intervals indicative of PEI that can be determined at step 210 were discussed above with reference to FIGS. 1A-1C, but embodiments of the present invention are not limited to such examples.

At step 212, the patient's PEI is monitored based on at least one determined interval indicative of PEI. Alternatively, in accordance with an embodiment, the patient's PEI is monitored based on the signal indicative of changes in arterial blood volume (e.g., the PPG/IPG signal) by, for example, monitoring changes in the temporal location of a predetermined feature of arterial blood volume. As discussed above, in accordance with an embodiment, the one or more predetermined features of the PPG/IPG signal can include the pulse foot of the PPG/IPG signal, the pulse peak of the PPG/IPG signal, and/or the maximum positive slope of the PPG/IPG signal. For each of a plurality of periods of time, the temporal location of one of the predetermined features of the PPG/IPG signal is detected. The patient's PEI is monitored based on the interval between the temporal location of one of the predetermined features of the PPG/IPG signal and a subsequent one of the predetermined features of the PPG/IPG signal.

In accordance with an embodiment, because implanted electrodes and an implanted sensor are used to determine the interval between the predetermined feature of the signal indicative of cardiac electrical activity and the predetermined feature of the signal indicative of changes in arterial blood volume, and/or the interval between the temporal location of one of the predetermined features of arterial blood volume and a subsequent one of the predetermined features of arterial blood volume, a patient's PEI can be monitored on a chronic basis. Thus, PEI can be tracked to monitor a patient's evolving cardiac health, and to trigger an alert, therapy and/or adjusting therapy based on the monitored PEI, as indicated at step 214. For example, in accordance with an embodiment, a change in a patient's activity, blood pressure (BP) and/or heart rate should result in a proportional change in the patient's PEI. If the patient's PEI does not change proportionally with the patient's activity, BP and/or heart rate, this can be indicative of disease and/or disease progression. Thus, an alert, therapy and/or adjusting therapy should be triggered.

In accordance with an embodiment, the duration of time that a patient's PEI exceeds or is below a PEI threshold can be monitored and tracked. If the patient's PEI exceeds and/or falls below the PEI threshold for a predetermined time (e.g., a day, a week or a month), this can be indicative of disease and/or disease progression. Similarly, if the patient's PEI exceeds and/or falls below the PEI threshold by a certain amount and/or percentage of the PEI threshold, this can also be indicative of disease and/or disease progression; and an alert, therapy and/or adjusting therapy should be triggered.

In accordance with an embodiment, an alert triggering mechanism can be part of an implanted system. Alternatively, an implanted system can trigger a non-implanted alarm of a non-implanted system. In still other embodiments, where PEI information is transmitted, e.g., via telemetry to an external device, a non-implanted alert can be triggered.

In an embodiment, use of various thresholds can be used to trigger alarms and/or therapy. For example, depending on the frequency, periodic monitoring of PEI may be costly in terms of energy, memory and/or processing resources. Accordingly, it may be more efficient to trigger the performance of certain steps upon detection of an event, such as a specific activity, or lack thereof, and/or a specific posture of the patient. For example, an activity sensor and/or posture sensor (e.g., sensor 415 in FIG. 4) can be used to trigger the performance of steps of FIG. 2A. For example, the steps of FIG. 2A can be triggered when it is detected that a patient is inactive and lying down. Additionally, or alternatively, such steps can be triggered when a patient is upright and walking. In still other embodiments, such steps can be triggered to occur, at specific intervals following a patient changing their posture (e.g., assuming an upright posture, or lying down) and/or activity level. For example, following a triggering event, intervals indicative of PEI can be determined once a minute for 10 minutes, or at 1 minute, 2 minutes, 5 minutes and 10 minutes after the triggering event. Of course, other variations are also possible, and within the scope of the present invention. It may also be that one or more specific step is performed substantially continually, but other steps are only performed in response to a triggering event or on demand.

Where at least some of steps of FIG. 2A are triggered in response to detection of various different activity and/or posture states, information about the patient's activity and/or posture can also be stored along with the patient's PEI, so that such information can be correlated. In other words, there could be a cross-correlation of PEI intervals with levels of activity and/or posture.

Referring to step 214, therapy can include delivering or instructing the taking of medication and/or adjusting device parameters. In the case of adjusting device parameters, parameters can be adjusted to minimize PEI. Additionally, upon determining the patient's PEI for each of a plurality of different electrode configurations, an electrode configuration can be selected based on the determined PEIs. For example, in accordance with embodiments of the present invention, an electrode configuration can be selected that provides a minimum PEI.

Additionally, or alternatively, at step 216, information indicative of the monitored PEI, and potentially other information, can be stored within memory of the implantable system for later analysis within the device and/or for later transmission to an external device. Such an external device (e.g., an external programmer or external monitor) can then be used to analyze such data.

In accordance with specific embodiments, when monitoring a patient's PEI, the one or more intervals indicative of PEI determined at step 210 can be affected by the patient's hemodynamics, and/or the location of the implanted sensor used to detect the one or more predetermined features of the signal indicative of changes in arterial blood volume, and/or the patient's heart rate. With respect to the location of the implanted sensor, as discussed above, PEI is the interval from the onset of cardiac electrical activity to the pressure pulse reaching the aorta. More specifically, in accordance with an embodiment of the present invention, one or more intervals indicative of PEI is/are determined by determining a time from one of the predetermined features of the signal indicative of cardiac electrical activity (e.g., ECG/IEGM signal) to one of the predetermined features of the signal (e.g., PPG/IPG signal) indicative of changes in arterial blood volume. It is preferred that the implanted sensor used to obtain the PPG/IPG signal be close to the patient's aorta to minimize the affect of the pulse transit time on the interval indicative of PEI; however, this may not always be possible. As such, because the implanted sensor used to obtain the PPG/IPG signal may be located some distance from the aorta, there could be a delay from the onset of cardiac electrical activity to when the pressure pulsation signal arrives at the PPG/IPG sensor, and if a patient's actual PEI is to be obtained, the patient's PEI should be adjusted for this delay (hereinafter referred to as transit time).

A patient's hemodynamics can also affect the one or more intervals indicative of PEI. As discussed above, the transit time of the signal indicative of changes in arterial blood volume can affect the measurement of a patient's PEI, and a patient's hemodynamics can affect the transit time, thereby affecting the interval indicative of PEI. For example, a patient having steady blood pressure would expect a relatively consistent interval indicative of PEI, since the time it takes the pressure pulse to reach the PPG/IPG sensor would remain relatively the same. However, if a patient has steady blood pressure, but a PEI that is changing more than a predetermined amount, this would be indicative of decreasing cardiac health.

In accordance with another embodiment, as blood pressure increases, the time it takes for the pressure pulse to reach the PPG/IPG sensor decreases, and thus, results in a shorter transit time. Alternatively, as blood pressure decreases, the time it takes for the pressure pulse to reach the PPG/IPG sensor increases, and a longer transit time would result. In both situations, however, although the patient's actual PEI may have remained the same, the interval indicative of PEI would have changed (e.g., the interval indicative of PEI should have decreased for increased blood pressure and increased for decreased blood pressure) because the transit time has changed.

Several techniques can be implemented to reduce the effect blood pressure and/or the location of the implanted PPG/IPG sensor has on the interval indicative of PEI. Assuming blood pressure has not changed during the interval indicative of PEI determined at step 210, the transit time can be obtained and factored out. In an embodiment, the transit time can be obtained during implant using an invasive pressure catheter. The transit time can then be factored out of the interval indicative of PEI determined at step 210 to obtain an actual measure of PEI. In an alternate embodiment, two implanted sensors can be used to determine the transit time, and once the transit time is determined, the transit time can be factored out of the interval indicative of PEI to obtain the actual PEI. This can be accomplished by first determining the distance between the two sensors (the sensors used to measure transit time). This can be determined, for example, at the time the sensors are implanted. Then, for each interval indicative of PEI, the pulse transit time between the two sensors is determined by obtaining a first measure of time as the pressure pulse reaches the first sensor, obtaining a second measure of time as the pressure pulse reaches the second sensor, and taking the difference in time between the first measure of time and the second measure of time to determine the pulse transit time. The pulse transit time between these two sensors can be used to determine the delay between the onset of cardiac electrical activity to when the pressure pulse reaches the PPG/IPG sensor.

The next step is to determine the transit time of the pressure pulse that reaches the PPG/IPG sensor. This requires determining the pulse velocity of the pressure pulse that reaches the PPG/IPG sensor and the transit time of the pressure pulse to travel from the aorta to the PPG/IPG sensor. The velocity of the pulse can be determined by dividing the distance between the two sensors by the pulse transit time determined above.

The velocity is then used to determine the transit time affecting the PPG/IPG sensor reading by determining the distance from the PPG/IPG sensor to the aorta, and then dividing the distance between the aorta and the PPG/IPG sensor by the above obtained velocity. The distance between the aorta and the PPG/IPG sensor can be determined at the time of implanting the PPG/IPG sensor. Actual PEI can then be calculated by determining the interval indicative of PEI at step 210, and then subtracting out the transit time.

If hemodynamics has changed, the interval indicative of PEI may need to be adjusted to reflect this. In accordance with an embodiment of the invention, this can be accomplished by obtaining a reading of blood pressure at a first interval indicative of PEI, obtaining a second reading of blood pressure at a second interval indicative of PEI, and then determine the difference in blood pressure between the first interval and the second interval. The interval indicative of PEI can then be adjusted according to the measured difference in blood pressure. Exemplary techniques for obtaining measures of blood pressure using an IEGM/ECG signal and/or a PPG/IPG signal are disclosed in the following patent applications, each of which is incorporated herein by reference: U.S. patent application Ser. No. 11/848,586, filed Aug. 31, 2007, entitled "Implantable Systemic Blood Pressure Measurement Systems and Methods" (Attorney Docket No. A07P3032); and U.S. patent application Ser. No. 12/637,574, filed Dec. 14, 2009, entitled "Arterial Blood Pressure Monitoring Devices, Systems and Methods for Use While Pacing" (Attorney Docket No. A09P3006).

In accordance with an embodiment, when monitoring a patient's PEI, the one or more intervals indicative of PEI determined at step 210 can be affected by the patient's heart rate. As described above, PEI is the interval from the onset of cardiac electrical activity to the pressure pulse reaching the aorta. This interval can change depending on whether the patient's heart rate has increased or decreased, where an increase in heart rate can result in a shorter interval indicative of PEI, and a decrease in heart rate can result in a longer interval indicative of PEI. Thus, because the patient's PEI is sensitive to the patient's heart rate, and PEI is used to access cardiac functionality of the patient, the interval indicative of PEI should account for changes in the patient's heart rate.

Techniques can be implemented to lessen the effect the patient's heart rate has on the interval indicative of PEI. In accordance with an embodiment, a patient's PEI can be monitored as described in steps, 202, 204, 206, 208 and 210 for a range of heart rates, and stored in a table or other format that can be accessed. The range of heart rates can be relatively small or expansive. For example, PEI can be measured for each heart rate (e.g., 60, 61, 62, etc. beats per minute (BPM)), for a range of heart rates (e.g., 60-69, 70-79, etc. BPM), or some other predetermined range of heart rates. To determine whether a patient's PEI has reduced or increased, the patient's measured PEI is compared to PEI values monitored for the same heart rate or range of heart hearts that have been stored in, for example, the lookup table.

In an alternative embodiment, rather than store, for a range of heart rates, the one or more intervals indicative of PEI determined at step 210 into a lookup table, PEI can be normalized based on the patient's heart rate. For example, it is known that as HR increases, the interval between the predetermined feature of the signal indicative of cardiac electrical activity and the predetermined feature of the signal indicative of changes in arterial blood volume decreases. To compare a patient's PEI at different heart rates, the measure of the interval indicative of PEI can be normalized. As such, to determine whether a patient's PEI has reduced or increased, the patient's current normalized PEI is compared to previously determined PEI values that have also been normalized.

An exemplary calibration procedure (performed at implant and/or thereafter) will now be explained. During the calibration procedure, actual measures of arterial blood pressure (e.g., systolic blood pressure) are measured using any known accurate acute technique, and an interval indicative of PEI is monitored for in a manner described above using an implanted device. The actual measure(s) of the patient's systolic blood pressure can be obtained, e.g., using a non-invasive auscultatory or oscillometric techniques, or an invasive intravascular cannula method, or any other acute technique. For a more specific example, actual arterial blood pressure measurements (e.g., SBP and DBP) can be measured using a high fidelity micronometer-tipped pressure catheter (e.g., model 4F, SPC-120, available from Millar Instruments, Texas), which is placed in the ascending aorta via a carotid arteriotomy.

Still referring to the calibration procedure, during a first one of the periods of time determined at step 210, a first measure of systolic blood pressure is obtained, and during a second one of the periods of time determined at step 210, a second measure of systolic blood pressure is obtained. When monitoring changes in the patient's PEI from the first period of time to the second period of time, the interval corresponding to the second period of time is calibrated based on the change in the measure of systolic blood pressure from the first period of time to the second period of time, if any change.

Figure 2B:
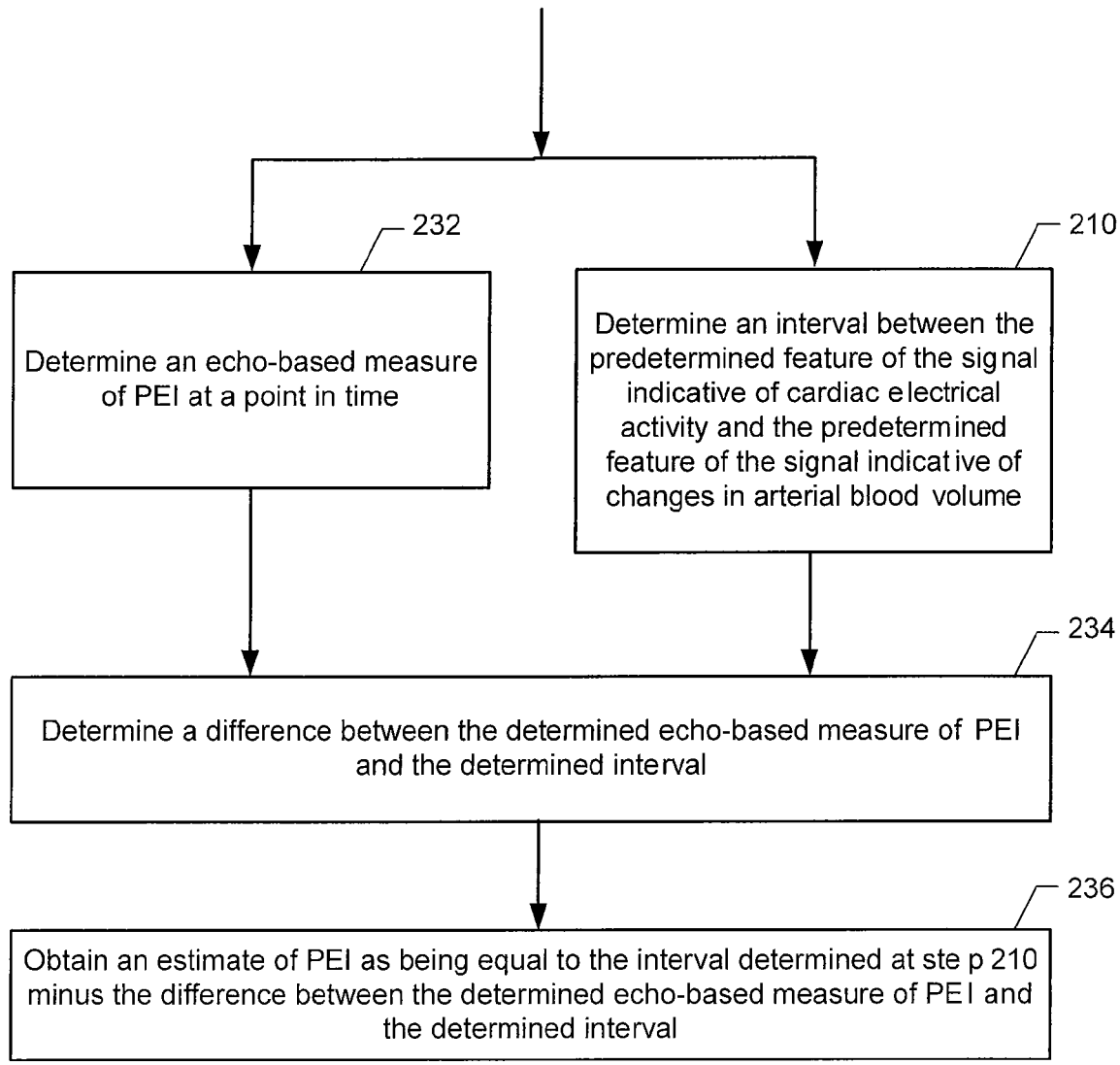
FIG. 2B is a high level flow diagram that is used to explain embodiments of the present invention that can be used to estimate PEI upon determining an echo-based measure of PEI.

FIG. 2B is a high level flow diagram that is used to explain embodiments of the present invention that can be used to estimate PEI upon determining an echo-based measure of pre-ejection interval (PEI) or any other gold standard measure of PEI. At step 232 an echo-based measure of PEI is determined at a point in time. At step 210, at about the same time, an interval is determined between the predetermined feature of the signal indicative of cardiac electrical activity and the predetermined feature of the signal indicative of changes in arterial blood volume. At step 234, a difference is determined between the determined echo-based measure of PEI and the determined interval. At step 236, an estimate of PEI is obtained as being equal to the interval determined at step 210 minus the difference between the determined echo-based measure of PEI and the determined interval. Other gold standard measures of PEI can be used in place of the echo based measure.

Embodiments of the present invention are not limited to the exact order and/or boundaries of the steps shown in FIGS. 2A and 2B. In fact, many of the steps can be performed in a different order than shown, and many steps can be combined, or separated into multiple steps. For another example, certain steps shown in the FIGS. 2A and 2B can be separated into two or more steps. The only time order is important is where a step acts on the results of a previous step.

As the term is being used herein, PEI is synonymous with pre-ejection period (PEP). Thus, a patient's PEP can be monitored using the embodiments of the present invention described above.

Exemplary Implantable System

Figure 3:
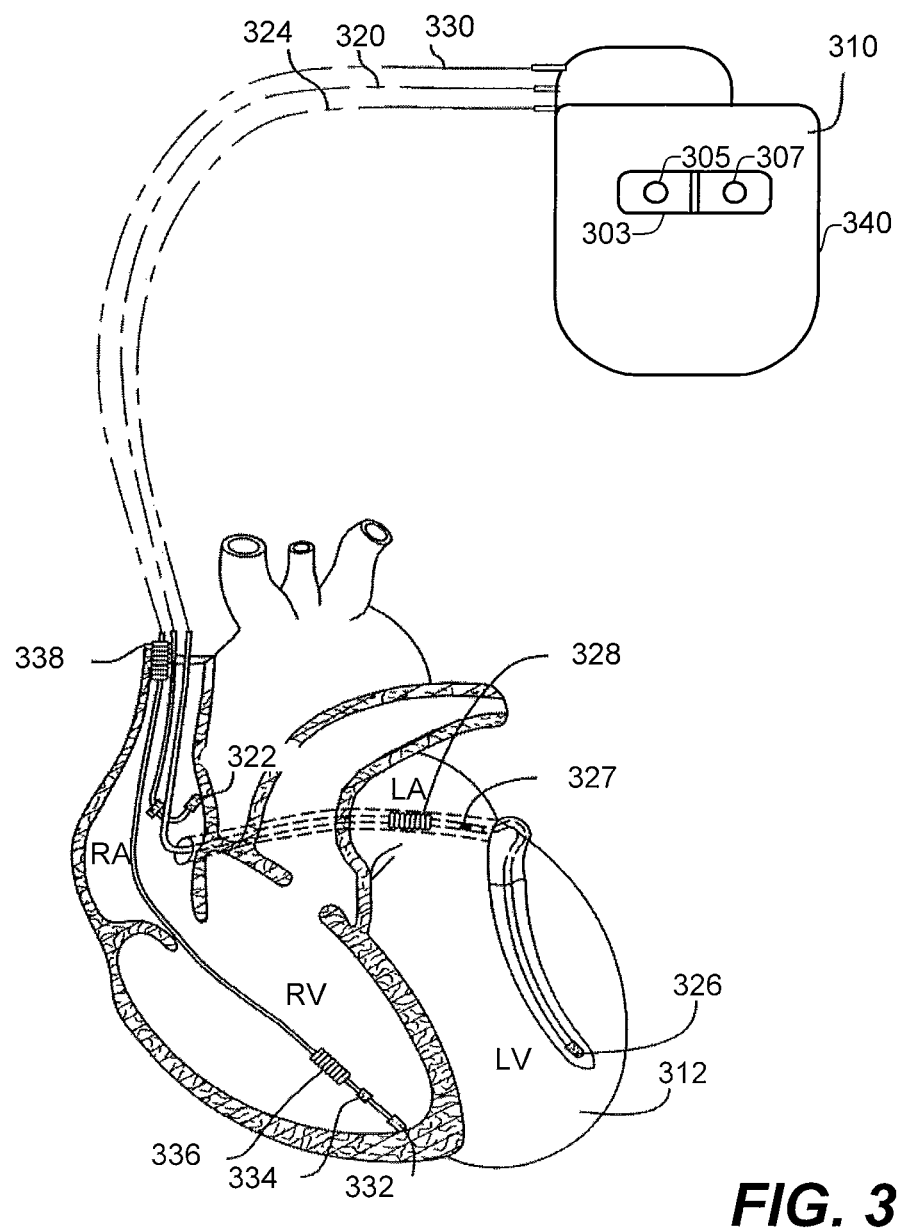
FIG. 3 illustrates an exemplary implantable cardiac stimulation device that includes a PPG sensor, and which can be used to perform various embodiments of the present invention.
Figure 4:
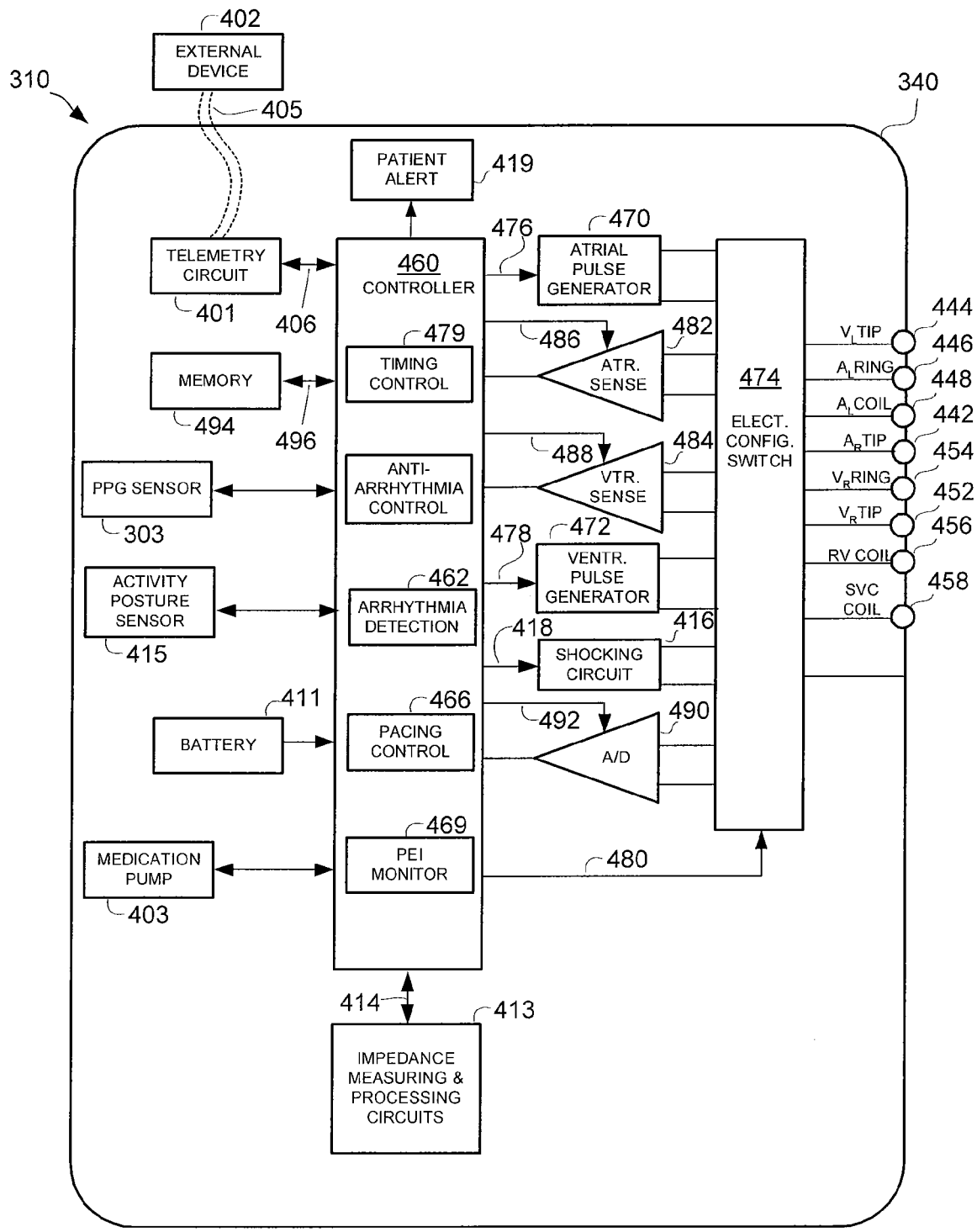
FIG. 4 is a simplified block diagram that illustrates possible components of the implantable device shown in FIG. 3.

FIGS. 3 and 4 will now be used to describe an exemplary implantable system that can be used to implement embodiments of the present invention including but not limited to monitoring a patient's pre-ejection interval (PEI). Referring to FIG. 3, the implantable system is shown as including an implantable stimulation device 310, which can be a pacing device and/or an implantable cardioverter defibrillator. The device 310 is shown as being in electrical communication with a patient's heart 312 by way of three leads, 320, 324 and 330, which can be suitable for delivering multi-chamber stimulation and shock therapy. The leads can also be used to obtain IEGM and/or IPG signals, for use in embodiments of the present invention. As described below, it is also possible that one of these leads (or another lead) can include an optical sensor (also referred to as a PPG sensor) that is useful for obtaining a PPG signal, similar to signal 104 shown in FIG. 1.

In FIG. 3, the implantable device 310 is shown as having a PPG sensor 303 (also referred to as an optical sensor) attached to its housing 340. The PPG sensor 303, which can be used to obtain a PPG signal similar to signal 104 shown in FIG. 1, includes a light source 305 and a light detector 307. The light source 305 can include, e.g., at least one light-emitting diode (LED), incandescent lamp or laser diode, but is not limited thereto. The light detector 307 can include, e.g., at least one photoresistor, photodiode, phototransistor, photodarlington or avalanche photodiode, but is not limited thereto. Light detectors are often also referred to as photodetectors or photocells.

The light source 305 outputs light that is reflected or back-scattered by surrounding patient tissue, and reflected/back-scattered light is received by the light detector 307. In this manner, changes in reflected light intensity are detected by the light detector, which outputs a signal indicative of the changes in detected light. The output of the light detector can be filtered and amplified. The signal can also be converted to a digital signal using an analog to digital converter, if the PPG signal is to be analyzed in the digital domain. A PPG sensor can use a single wavelength of light, or a broad spectrum of many wavelengths. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The PPG sensor 302 can be attached to a housing 340 of an implantable device, which as mentioned above can be, e.g., a pacemaker and/or an implantable cardioverter-defibrillator (ICD), or a simple monitoring device. Exemplary details of how to attach a sensor module to an implantable cardiac stimulation device are described in U.S. patent application Ser. No. 10/913,942, entitled "Autonomous Sensor Modules for Patient Monitoring" (Turcott et al.), filed Aug. 4, 2004 (Attorney Docket No. A04P3019-US1), which is incorporated herein by reference. It is also possible that the PPG sensor 302 be integrally part of the implantable cardiac stimulation device 310. For example, the PPG sensor 302 can be located within the housing 340 of an ICD (and/or pacemaker) that has a window through which light can be transmitted and detected. In a specific embodiment, the PPG sensor 302 has a titanium frame with a light transparent quartz or sapphire window that can be welded into a corresponding slot cut in the housing of the ICD. This will insure that the ICD enclosure with the welded PPG sensor will maintain a hermetic condition.

Where the PPG sensor is incorporated into or attached to a chronically implantable device 310, the light source 305 and the light detector 307 can be mounted adjacent to one another on the housing or header of the implantable device, or on the bottom of the device, or at any other location. The light source 305 and the light detector 307 can be placed on the side of the implantable device 310 that, following implantation, faces the chest wall, and are configured such that light cannot pass directly from the source to the detector. The placement on the side of the device 310 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 305 and the light detector 307 can be placed on the face of the device 310 that faces the skin of the patient. Other variations are also possible.

In an alternative embodiment, the PPG sensor 303 (or other plethysmography sensor) can be is remote from the housing 340 of the device 310, but communicates with the electronics in the device housing 340 via one or more wires, optical fibers, or wirelessly (e.g., using telemetry, RF signals and/or using body fluid as a communication bus medium). This embodiment enables an obtained PPG signal to be indicative of changes in arterial blood volume at a location remote from the patient's heart, where such location is also remote from the device housing 340. If desired, multiple PPG signals can be obtained, e.g., using multiple PPG sensors at different locations.

In another embodiment, optical fibers can be used to transmit light into and detect light from tissue that is remote from the device housing, even though the light source and light detector are located within or adjacent the device housing 340. This embodiment enables an obtained PPG signal to be indicative of changes in arterial blood volume at a location remote from the patient's heart, where such location is remote from the device housing 340, even though the light source 305 and light detector 307 are not remote from the housing. The distal end of the optical fiber(s) associated with the light source can be generally parallel to the distal end of the optical fiber(s) associated with the light detector, so that the light detector detects the portion of light reflected from tissue. Alternatively, the distal end of the optical fiber(s) associated with the light source can generally face the distal end of the optical fiber(s) associated with the light detector, with tissue therebetween, so that the light detector detects the portion of light transmitted through (as opposed to reflected from) the tissue therebetween.

In an embodiment, a PPG sensor can be within or attached to a lead that may extend from a main device housing 340. Accordingly, in this embodiment, a housing of the sensor module is sized to fit within the implantable lead. For example, the PPG can be located proximal from the distal tip of the lead so that the PPG sensor is sufficiently remote from the heart that variations in pulse transmission time are detectable and meaningful. The portion of the lead that is adjacent to a window of the PPG sensor module, where light is to exit and enter, should allow the light to pass in and out of the sensor. Thus, the lead may be transparent, or include its own window, opening, or the like. The lead can including tines for attaching the lead in its desired position, but may include any other type of fixation means (e.g., a pigtail shaped fixation means), or none at all. The lead can also have a suture sleeve, that enables the lead to be sutured to patient tissue. Additional details of a lead that includes an optical sensor that can be used to produce a PPG signal are provided in U.S. patent application Ser. No. 11/231,555, entitled "Improved Multi-Wavelength Implantable Oximeter Sensor" (Poore), filed Sep. 20, 2005 (Attorney Docket No. A05P1078), and U.S. patent application Ser. No. 11/282,198, entitled "Implantable Device with a Calibration Photodetector" (Poore), filed Nov. 17, 2005 (Attorney Docket No. A05P1078US01).

The implantable PPG sensor 303 obtains a PPG signal that after filtering is similar to signal 104 shown in FIG. 1, that pulsates over the cardiac cycle. Modulation of the signal occurs because arteries distend as the pressure wave created by the heart's pumping mechanism reaches the sensor site. Such a signal can be filtered and/or amplified as appropriate, e.g., to remove respiratory affects on the signal, and the like. Additionally, the signal can be digitized using an analog to digital converter. Exemplary techniques for performing filtering and other processing of a PPG signal (or other plethysmography signal) are explained with reference to FIGS. 5 and 6A-6E.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals. Further, as mentioned above, electrodes of the various leads can be used to obtain an IPG signal, and the IPG signal can be used in place of the PPG signal.

In specific embodiments, the plethysmography signal can be produced using non-radiant methods and devices, including, but not limited to mechanical strain, electrical impedance, or pressure. More specifically, rather than using a PPG sensor that includes a light source and detector, the implanted plethysmography sensor can include a strain gauge, a linear displacement sensor, or an ultrasound transducer, each of which is known in the art. Alternatively, an impedance plethysmography sensor, which is also known in the art, can be used. Details of exemplary implantable sensors that produce an impedance plethysmography signals are disclosed, e.g., in U.S. Pat. Nos. 4,674,518, 4,686,987 and 5,334,222 (all to Salo), which are incorporated herein by reference.

Still referring to FIG. 3, to sense atrial cardiac signals and to provide right atrial chamber stimulation therapy, the device 310 is coupled to an implantable right atrial lead 320 having at least an atrial tip electrode 322, which typically is implanted in the patient's right atrial appendage. To sense left atrial and ventricular cardiac signals and to provide left-chamber pacing therapy, the device 310 is coupled to a "coronary sinus" lead 324 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

The device 310 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode 336 will be positioned in the right ventricle and the SVC coil electrode 338 will be positioned in the superior vena cava. Accordingly, the right ventricular lead 330 is capable of receiving cardiac signals and delivering stimulation in the form of pacing and shock therapy to the right ventricle.

FIG. 4 will now be used to provide some exemplary details of the components of the implantable devices 310. Referring now to FIG. 4, the implantable devices 310, and alternative versions thereof, can include a microcontroller 460. As is well known in the art, the microcontroller 460 typically includes a microprocessor, or equivalent control circuitry, and can further include RAM and/or ROM memory, logic and timing circuitry, state machine circuitry and/or I/O circuitry. Typically, the microcontroller 460 includes the ability to process or monitor input signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing and data analysis functions are well known in the art. In specific embodiments of the present invention, the microcontroller 460 performs some or all of the steps associated with determining an interval used to monitor pre-ejection interval (PEI). Additionally, the microcontroller 460 may detect arrhythmias, and select and control delivery of anti-arrhythmia therapy.

Representative types of control circuitry that may be used with embodiments of the present invention include the microprocessor-based control system of U.S. Pat. No. 4,940,052 (Mann et. al.) and the state-machines of U.S. Pat. No. 4,712, 555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

Depending on implementation, the device 310 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation. For example, if the implantable device is a monitor that does not provide any therapy, it is clear that many of the blocks shown may be eliminated.

The housing 340, shown schematically in FIG. 4, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 can further include a connector (not shown) having a plurality of terminals, 442, 444, 446, 448, 452, 454, 456, and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 322.

To achieve left atrial and ventricular sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular tip electrode 326, the left atrial ring electrode 327, and the left atrial coil electrode 328, respectively.

To support right ventricle sensing, pacing and shocking, the connector further includes a right ventricular tip terminal ($V_R$ TIP) 452, a right ventricular ring terminal ($V_R$ RING) 454, a right ventricular shocking terminal ($R_V$COIL) 456, and an SVC shocking terminal (SVC COIL) 458, which are adapted for connection to the right ventricular tip electrode 332, right ventricular ring electrode 334, the RV coil electrode 336, and the SVC coil electrode 338, respectively.

An atrial pulse generator 470 and a ventricular pulse generator 472 generate pacing stimulation pulses for delivery by the right atrial lead 320, the right ventricular lead 330, and/or the coronary sinus lead 324 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuits 482 and ventricular sensing circuits 484 may also be selectively coupled to the right atrial lead 320, coronary sinus lead 324, and the right ventricular lead 330, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, band-pass filtering, and a threshold detection circuit, as known in the art, to selectively sense the cardiac signal of interest. The automatic gain control enables the device 310 to deal effectively with the difficult problem of sensing the low amplitude signal characteristics of atrial or ventricular fibrillation. Such sensing circuits, 482 and 484, can be used to determine cardiac performance values used in the present invention. Alternatively, an automatic sensitivity control circuit may be used to effectively deal with signals of varying amplitude.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 310 includes an arrhythmia detector 462 that utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation) can be classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 462 can perform arrhythmia discrimination, e.g., using measures of arterial blood pressure determined in accordance with embodiments of the present invention. The arrhythmia detector 462 can be implemented within the microcontroller 460, as shown in FIG. 4. Thus, this detector 462 can be implemented by software, firmware, or combinations thereof. It is also possible that all, or portions, of the arrhythmia detector 462 can be implemented using hardware. Further, it is also possible that all, or portions, of the ischemia detector 462 can be implemented separate from the microcontroller 460.

In accordance with an embodiment of the present invention, the implantable device 310 includes PEI monitor 469. PEI monitor 469 can be used to monitor the patient's PEI based on an interval, using the techniques described above. Such techniques can include detecting a predetermined feature of the signal indicative of cardiac electrical activity, detecting a predetermined feature of the signal indicative of changes in arterial blood volume, and then determining an interval between the predetermined feature of the signal indicative of cardiac electrical activity and the predetermined feature of the signal indicative of changes in arterial blood volume. PEI monitor 469 is also configured to monitor changes in the patient's PEI by monitoring changes in the interval over time, and/or store, within the implantable system, information indicative of the monitored PEI so that the stored information is available for transfer to a non-implanted system. Based on these changes in the patient's PEI, PEI monitor 469 can trigger an alert, therapy and/or adjusting therapy.

In an embodiment, PEI monitor 469 can be configured to receive an echo-based measure of PEI determined at a point in time. For about the same that the echo-based measure of PEI is determined, an interval is determined between the predetermined feature of the signal indicative of cardiac electrical activity and the predetermined feature of the signal indicative of changes in arterial blood volume. Once a difference between the determined echo-based measure of the PEI and the determined interval is determined by PEI monitor 469, the patient's PEI is estimated as being equal to the interval between the predetermined feature of the signal indicative of cardiac electrical activity and the predetermined feature of the signal indicative of changes in arterial blood volume, minus the determined difference.

PEI monitor 469 can be implemented within the microcontroller 460, as shown in FIG. 4, and can be implemented by software, firmware, or combinations thereof. It is also possible that all, or portions of PEI monitor 469 can be implemented separate from microcontroller 460.

The implantable device 310 can also include a pacing controller 466, which can adjust a pacing rate and/or pacing intervals based the interval indicative of PEI, in accordance with embodiments of the present invention. The pacing controller 466 can be implemented within the microcontroller 460, as shown in FIG. 4. Thus, the pacing controller 466 can be implemented by software, firmware, or combinations thereof. It is also possible that all, or portions, of the pacing controller 466 can be implemented using hardware. Further, it is also possible that all, or portions, of the pacing controller 466 can be implemented separate from the microcontroller 460.

The implantable device can also include a medication pump 403, which can deliver medication to a patient if the patient's PEI falls outside certain thresholds or ranges, as described in step 214. Information regarding implantable medication pumps may be found in U.S. Pat. No. 4,731,051 (Fischell) and in U.S. Pat. No. 4,947,845 (Davis), both of which are incorporated by reference herein.

Still referring to FIG. 4, cardiac signals are also applied to the inputs of an analog-to-digital (A/D) data acquisition system 490. The data acquisition system 490 can be configured to acquire various signal, including but not limited to, CI, IEGM, PPG and IPG signals, convert the raw analog data into a digital signal, and store the digital signals for later processing and/or telemetric transmission to an external device 402. The data acquisition system 490 can be coupled to the right atrial lead 320, the coronary sinus lead 324, and the right ventricular lead 330 through the switch 474 to sample cardiac signals across any pair of desired electrodes.

The data acquisition system 490 can be coupled to the microcontroller 460, or other detection circuitry, for detecting an evoked response from the heart 312 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 460 is further coupled to the memory 494 by a suitable data/address bus 496, wherein the programmable operating parameters used by the microcontroller 460 are stored and modified, as required, in order to customize the operation of the implantable device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy. The memory 494 can also store data including information about the patient's PEI based on the interval.

The operating parameters of the implantable device 310 may be non-invasively programmed into the memory 494 through a telemetry circuit 401 in telemetric communication with an external device 402, such as a programmer, transtelephonic transceiver, or a diagnostic system analyzer. The telemetry circuit 401 can be activated by the microcontroller 460 by a control signal 406. The telemetry circuit 401 advantageously allows intracardiac electrograms and status information relating to the operation of the device 310 (as contained in the microcontroller 460 or memory 494) to be sent to the external device 402 through an established communication link 404. The telemetry circuit can also be use to transmit arterial blood pressure data to the external device 402.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 310 additionally includes a battery 411 which provides operating power to all of the circuits shown in FIG. 4. If the implantable device 310 also employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected.

The implantable device 310 is also shown as including an activity and/or posture sensor 415. Such a sensor 415 can be a simple one dimensional sensor that converts mechanical motion into a detectable electrical signal, such as a back electro magnetic field (BEMF) current or voltage, without requiring any external excitation. Alternatively, the sensor 415 can measure multi-dimensional activity information, such as two or more of acceleration, direction, posture and/or tilt. Examples of multi-dimensional activity sensors include, but are not limited to: the three dimensional accelerometer-based position sensor disclosed in U.S. Pat. No. 6,658,292 to Kroll et al., which is incorporated herein by reference; the AC/DC multi-axis accelerometer disclosed in U.S. Pat. No. 6,466,821 to Pianca et al., which in incorporated herein by reference; and the commercially available precision dual-axis accelerometer model ADXL203 and three-axis accelerometer model ADXL346, both available from Analog Devices of Norwood, Mass.

The implantable device 310 can also include a magnet detection circuitry (not shown), coupled to the microcontroller 460. It is the purpose of the magnet detection circuitry to detect when a magnet is placed over the implantable device 310, which magnet may be used by a clinician to perform various test functions of the implantable device 310 and/or to signal the microcontroller 460 that the external programmer 402 is in place to receive or transmit data to the microcontroller 460 through the telemetry circuits 401.

As further shown in FIG. 4, the device 310 is also shown as having an impedance measuring and processing circuit 413 which is enabled by the microcontroller 460 via a control signal 414 and can be used for obtaining many types of bodily and intracardiac impedances, including a network of single- or multi-vector impedance measurements. Such impedance measurements can be used, e.g., for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 413 may be coupled to the switch 474 so that any desired electrodes may be used, and networks of vectors can be selected.

In the case where the implantable device 310 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (11 to 40 Joules), as controlled by the microcontroller 460. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 340 may act as an active electrode in combination with the RV electrode 336, or as part of a split electrical vector using the SVC coil electrode 338 or the left atrial coil electrode 328 (i.e., using the RV electrode as a common electrode).

The above described implantable device 310 was described as an exemplary pacing device. One or ordinary skill in the art would understand that embodiments of the present invention can be used with alternative types of implantable devices. Accordingly, embodiments of the present invention should not be limited to use only with the above described device.

Processing of Plethysmography Signals

Photoplethysmography (PPG) and Impedance Plethysmography signals (collectively referred to as PPG/IPG signals), and other plethysmography signals, show changes in a patient's arterial system as a result of the patient's heart contracting, and such signals are indicative of changes in arterial blood volume. A PPG signal can be obtained using a PPG sensor, which as explained above, can be an optical sensor including a light source and a light detector. An IPG signal can be obtained using an IPG sensor, which as explained above, can include electrodes and circuitry used to measure the impedance between such electrodes. One or more such electrodes can be located on one or more leads, and/or a mechanical housing of an implanted device can act as one of the electrodes.

When a PPG/IPG sensor is implanted at a location remote from the patient's heart, an obtained pressure pulsation signal has been shown to arrive from the heart to the PPG/IPG sensor after an amount of time that is related to arterial blood pressure. The velocity of the pressure pulsation traversing the arteries is positively correlated with systolic blood pressure, and thus, the location of the PPG/IPG sensor may affect the interval indicative of PEI. For example, PEI can be determined by determining a time from a paced cardiac event to one or more predetermined features of a signal indicative of changes in arterial blood volume. The predetermined features of the signal indicative of changes in arterial blood volume can be determined by using a PPG/IPG sensor to detect a pressure pulse that transcends from the left ventricle (LV) to the location of the PPG/IPG sensor. However, as blood pressure increases, the time it takes for the pressure pulse to reach the PPG/IPG sensor decreases. Alternatively, as blood pressure decreases, the time it takes for the pressure pulse to reach the PPG/IPG sensor increases. Thus, depending on a patient's blood pressure, the time from a paced cardiac event to one or more predetermined features of a signal indicative of changes in arterial blood volume could change.

Better estimates of PEI can be obtained depending on the location of the PPG/IPG sensor to the LV. Accordingly, to minimize the change in time for a paced cardiac event to one or more predetermined features of the signal indicative of arterial blood volume do to a change in blood pressure, the sensor used (e.g., PPG/PG sensor) to detect the signal indicative of changes in arterial blood volume should be placed as close to the LV as possible. A sensor placed close to the LV would be minimally affected by a change in pressure, and thus, better estimates of the interval indicative of PEI can be obtained.

Additionally, better estimates of PEI can be obtained if the PPG/IPG signals used in the above described embodiments are appropriately processed. Accordingly, certain embodiments of the present invention relate to techniques for processing PPG/IPG signals (or other plethysmography signals), as described below. Further embodiments of the present invention, described below, relate to how to extract features of PPG/IPG signals (or other plethysmography signals), which features can be used to determine the interval indicative of PEI, in the manners explained above.

Figure 5:
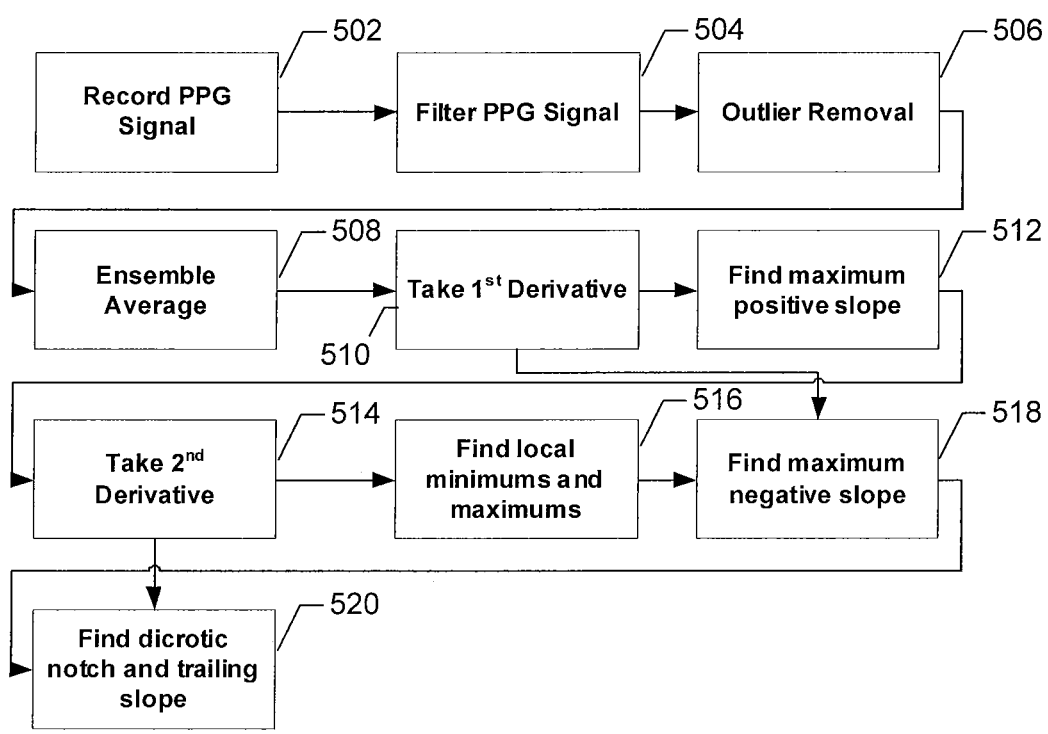
FIG. 5 is a flow diagram that is used to describe how features of a PPG or IPG signal can be detected in accordance with specific embodiments of the present invention.
Figure 6A:
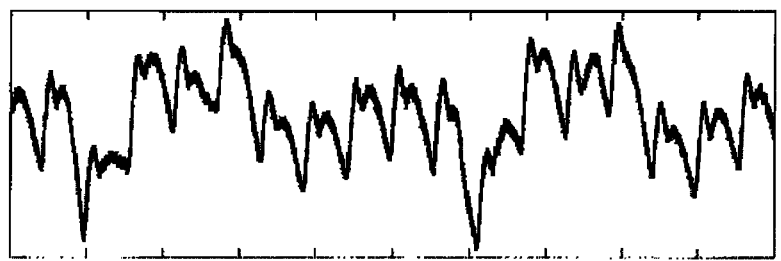
FIG. 6A illustrates an exemplary raw PPG signal over 20 seconds.

FIGS. 5 and 6A-6E will now be used to describe exemplary embodiments for obtaining a PPG signal and detecting predetermined features of the PPG signal. Similar techniques can be used to obtain an IPG signal (or other plethysmography signal) and detect predetermined features of the IPG signal (or other plethysmography signal). Referring to FIG. 5, at step 502 a PPG signal is recorded. Recording of a PPG signal may be triggered, e.g., on an R wave, based on respiratory cycle, based on activity levels, etc. An exemplary raw PPG signal recorded over 20 second is shown in FIG. 6A.

Figure 6B:
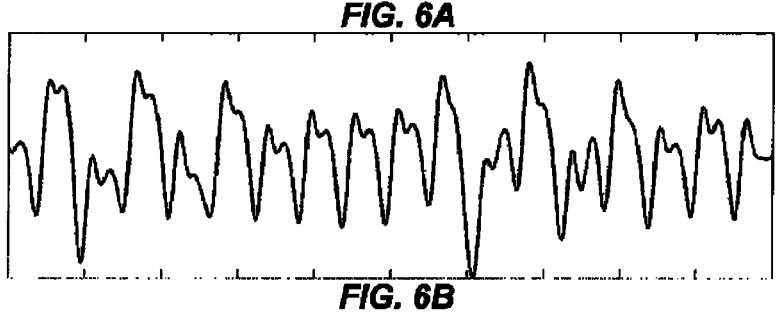
FIG. 6B illustrates the PPG signal of FIG. 6A after it has been band-passed filtered, which caused a reduction in noise due to respiration, high frequency noise, and motion artifacts.

At step 504, the PPG signal is filtered to remove respiratory noise, motion artifact, baseline drift, etc. For example, the signal can be band-pass filtered so that the pass-band is from about 0.7 to 10 Hz, although other pass bands can be used. FIG. 6B shows the raw PPG signal of FIG. 6A, after being band-passed filtered using a pass-band of about 0.7 to 10 Hz. As can be appreciated from FIG. 6B, most of the respiration signal and high frequency noise is removed by the filtering.

Figure 6C:
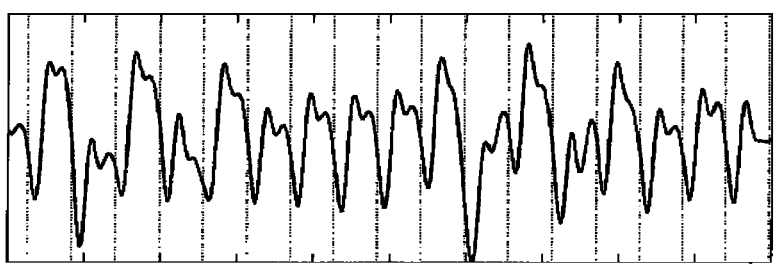
FIG. 6C is the same as FIG. 6B, but with R-wave markers added as vertical dashed lines.
Figure 6D:
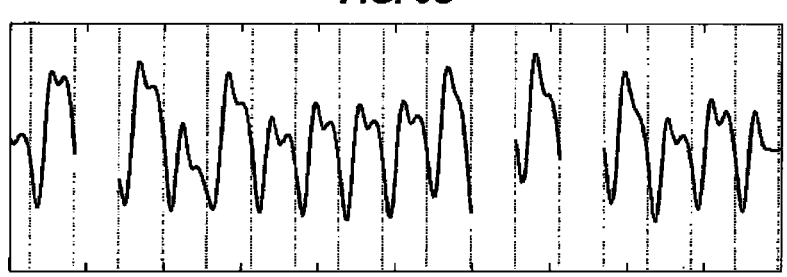
FIG. 6D is similar to FIG. 6C, but shows the removal of three outlier beats.

At step 506, an outlier removal process is performed, to remove "bad" heart beats. In an embodiment, the outlier removal can be accomplished by grouping a plurality (e.g., 20) consecutive heart beats, determining a mean of the filtered PPG signal for the plurality of heart beats, and then comparing the determined mean to individual cycles of the filtered PPG signal. Further, outlier removal can be performed by removing each cardiac cycle of the filtered PPG signal that deviates by at least a threshold amount (e.g., 3 or some other number of standard deviations) from the mean of the PPG signal for the plurality of consecutive beats. FIG. 6C show the filtered signal of FIG. 6B with R-wave markers added (shows as dashed vertical lines). FIG. 6D shows the filtered signal of FIGS. 6B and 6C with 3 "bad" beats removed as a result of an outlier removal process.

Figure 6E:
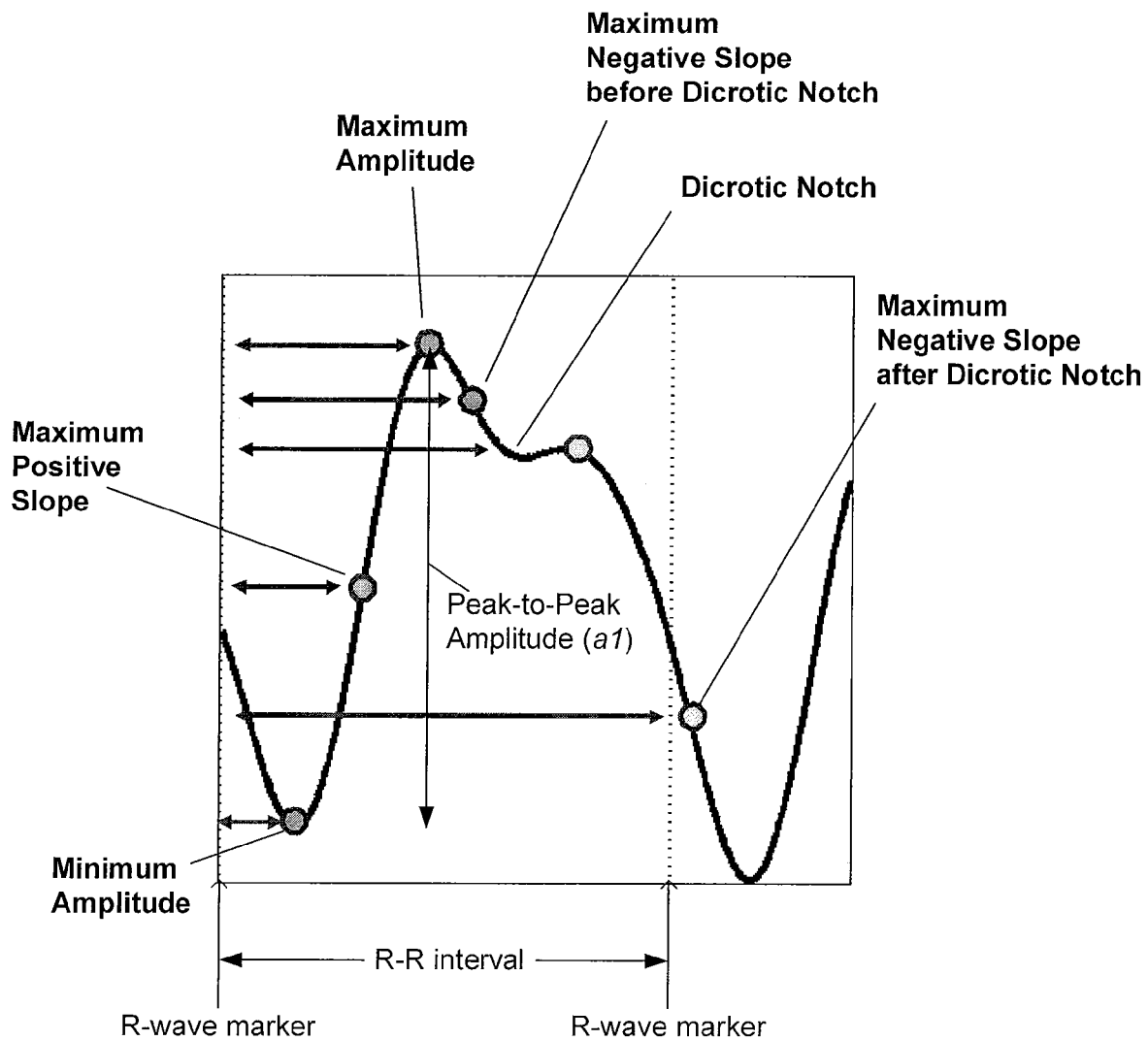
FIG. 6E illustrates an averaged PPG signal resulting from ensemble averaging the remaining cycles of FIG. 6D, and illustrates various feature of the PPG signal that can be determined and used with embodiments of the present invention.

Still referring to FIG. 5, at step 508, the cycles of the PPG signal remaining after the outlier removal step are then ensemble averaged. The result is an average representation of the PPG signal for the plurality of consecutive beats, with noise and "bad" beats removed. FIG. 6E shows an exemplary ensemble averaged PPG signal.

Thereafter, features of the PPG signal can be detected from the ensemble-averaged PPG signal. For example, as indicated at steps 510 and 512, the first derivative of the ensemble-averaged PPG signal can be determined, and the location of the maximum positive slope of the ensemble-averaged PPG signal can be detected by determining the maximum of the first derivative. Further, since it is believed that the maximum positive slope cannot be more than 70% of an R-R interval away from an R-wave, if the location of the maximum positive slope is not within 70% of an R-R interval away from an R wave, a maximum positive slope detection can be determined to be bad, and not be used.

As indicated at steps 514 and 516, the second derivative of the ensemble averaged PPG signal can be determined to find local minima and maxima. The locations of a maximum and a minimum are where the first derivative is equal to zero. The second derivative can be used to determine if a specific location is a maximum or a minimum. More specifically, if the second derivative is positive, then the point is at a minimum. If the second derivative is negative at a point, then the point is a maximum. The local minimum and local maximum that are closest to the maximum positive slope are the minimum and maximum amplitudes of the signal, which can be used, e.g., to determine the peak-to-peak amplitude of the ensemble averaged PPG signal. Further, as indicated at step 518, the maximum negative slope can be determined by identifying, from the first derivative, the local maximum that occurs after the maximum of the averaged PPG signal, but before the subsequent R-wave. As indicated at step 520, from the second derivative, the dicrotic notch can be identified by identifying the local minimum following the maximum of the averaged PPG signal, but before the subsequent R-wave. FIG. 6E shows examples of various predetermined features that can be detected. As shown in FIG. 6E a maximum downward slope can be detected prior to the dicrotic notch, as well as after the dicrotic notch.

Alternative techniques for detecting predetermined features of a PPG signal (or IPG signal) can be used, such as, but not limited to, techniques that rely on template matching, wavelets, neural networks, Fast Fourier Transform (FFT) and/or time warping. Alternatively, or additionally, techniques for detecting predetermined features of a PPG signal (or IPG signal) can utilize respiratory cycles and R-R intervals.

In certain embodiments, since the presence of the dicrotic notch comes and goes under different conditions, monitoring such conditions can use the presence of the dicrotic notch as a binary feature.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 2A and 2B. Further, it is possible to change the order of some of the steps shown in FIGS. 2A and 2B, without substantially changing the overall events and results. For another example, it is possible to change the boundaries of some of the blocks shown in FIG. 4.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with an implantable system, a method for monitoring a patient's pre-ejection interval (PEI), the method comprising:
   (a) using one or more electrodes implanted within and/or on the patient's heart to obtain a signal indicative of cardiac electrical activity;
   (b) using an implanted sensor to obtain a signal indicative of changes in arterial blood volume;
   (c) detecting a predetermined feature of the signal indicative of cardiac electrical activity;
   (d) detecting a predetermined feature of the signal indicative of changes in arterial blood volume;
   (e) determining an interval between the predetermined feature of the signal indicative of cardiac electrical activity and the predetermined feature of the signal indicative of changes in arterial blood volume;
   (f) determining a transit time representing at least one of i) a delay from an onset of the signal indicative of cardiac electrical activity obtained at the one or more electrodes to when the signal indicative of changes in arterial blood volume arrives at the implanted sensor or ii) a time for a pressure pulse to travel from an aorta to the implanted sensor; and
   (g) monitoring the patient's PEI based on the interval and the transit time.

2. The method of claim 1, further comprising:
   (g) triggering an alert, triggering therapy and/or adjusting therapy based on the monitored PEI.

3. The method of claim 1, further comprising:
   (g) storing, within the implantable system, information indicative of the monitored PEI so that the stored information is available for transfer to a non-implanted system.

4. The method of claim 1, wherein:
   steps (a), (b), (c), (d) and (e) are performed for each of a plurality of periods of time to thereby determine, for each of the plurality of periods of time, the interval between the predetermined feature of the signal indicative of cardiac electrical activity and the predetermined feature of the signal indicative of changes in arterial blood volume; and
   step (g) comprises monitoring changes in the patient's PEI based on changes in the interval over time.

5. The method of claim 4, further comprising:
   (h) triggering an alert, triggering therapy and/or adjusting therapy based on the monitored changes in PEI.

6. The method of claim 4, further comprising:
   (h) monitoring for an indication of disease and/or disease progression based on the monitored changes in the patient's PEI.

7. The method of claim 1, wherein:
   step (c) comprises detecting a predetermined feature indicative of ventricular depolarization of the signal indicative of cardiac electrical activity;

step (d) comprises detecting a predetermined feature corresponding to a systolic portion of the signal indicative of changes in arterial blood volume;

step (e) comprises detecting an interval between the predetermined feature indicative of ventricular depolarization of the signal indicative of cardiac electrical activity and the predetermined feature corresponding to a systolic portion of the signal indicative of changes in arterial blood volume; and step (g) comprises monitoring the patient's PEI based on the interval between the predetermined feature indicative of ventricular depolarization of the signal indicative of cardiac electrical activity and the predetermined feature corresponding to a systolic portion of the signal indicative of changes in arterial blood volume.

8. The method of claim 1, wherein:

step (a) comprises using one or more electrodes implanted within and/or on the patient's heart to obtain an intracardiac electrogram (IEGM) signal or an electrocardiogram (ECG) signal indicative of cardiac electrical activity; and step (b) comprises using an implanted photoplethysmography (PPG) sensor to obtain a photoplethysmography (PPG) signal indicative of changes in arterial blood volume, or using or an impedance plethysmography (IPG) sensor to obtain an impedance plethysmography (IPG) signal indicative of changes in arterial blood volume.

9. The method of claim 1, wherein the monitoring further comprises factoring the transit time out of the interval when monitoring the patient's PEI.

10. For use with an implantable system, a method for monitoring a patient's pre-ejection interval (PEI), the method comprising:

(a) using one or more electrodes implanted within and/or on the patient's heart to obtain a signal indicative of cardiac electrical activity;

(b) using an implanted sensor to obtain a signal indicative of changes in arterial blood volume;

(c) detecting a predetermined feature of the signal indicative of cardiac electrical activity;

(d) detecting a predetermined feature of the signal indicative of changes in arterial blood volume;

(e) determining an interval between the predetermined feature of the signal indicative of cardiac electrical activity and the predetermined feature of the signal indicative of changes in arterial blood volume; and (f) monitoring the patient's PEI based on the interval, wherein:

during a first one of the periods of time that steps (a), (b), (c), (d) and (e) are performed, a first measure of systolic blood pressure is obtained;

during a second one of the periods of time that steps (a), (b), (c), (d) and (e) are performed, a second measure of systolic blood pressure is obtained; and at step (f), when monitoring changes in the patient's PEI from the first period of time to the second period of time, calibrating the interval corresponding to the second period of time based on the change in the measure of systolic blood pressure from the first period of time to the second period of time, if any change.

11. For use with an implantable system, a method for monitoring a patient's pre-ejection interval (PEI), the method comprising:

(a) using one or more electrodes implanted within and/or on the patient's heart to obtain a signal indicative of cardiac electrical activity;

(b) using an implanted sensor to obtain a signal indicative of changes in arterial blood volume;

(c) detecting a predetermined feature of the signal indicative of cardiac electrical activity;

(d) detecting a predetermined feature of the signal indicative of changes in arterial blood volume;

(e) determining an interval between the predetermined feature of the signal indicative of cardiac electrical activity and the predetermined feature of the signal indicative of changes in arterial blood volume;

(f) monitoring the patient's PEI based on the interval, (g) performing a calibration including:

(g1) determining an echo-based measure of PEI at a point in time, (g2) at about the same point in time that the echo-based measure of PEI is determined, performing steps (a), (b), (c), (d) and (e) to determine an interval between the predetermined feature of the signal indicative of cardiac electrical activity and the predetermined feature of the signal indicative of changes in arterial blood volume, and (g3) determining a difference between the determined echo-based measure of PEI and the determined interval;

wherein when step (f) is performed after the calibration is performed, the patient's PEI is estimated based on the interval determined at step (e) and the difference determined during calibration.

12. The method of claim 11, wherein:

when step (f) is performed after the calibration is performed, the patient's PEI is estimated as being equal to the interval determined at step (e) minus the difference determined during calibration.

13. An implantable system capable of monitoring a patient's pre-ejection interval (PEI), comprising one or more electrodes configured to obtain a signal indicative of cardiac electrical activity;

an implantable sensor configured to obtain a signal that is indicative of changes in arterial volume;

a PEI monitor configured to detect a predetermined feature of the signal indicative of cardiac electrical activity, detect a predetermined feature of the signal indicative of changes in arterial blood volume, determine an interval between the predetermined feature of the signal indicative of cardiac electrical activity and the predetermined feature of the signal indicative of changes in arterial blood volume, determine a transit time representing at least one of i) a delay from an onset of the signal indicative of cardiac electrical activity obtained at the one or more electrodes to when the signal indicative of changes in arterial blood volume arrives at the implanted sensor or ii) a time for a pressure pulse to travel from an aorta to the implanted sensor; and monitor the patient's PEI based on the interval and the transit time.

14. The implantable system of claim 13, wherein the PEI monitor is configured to trigger an alert, therapy and/or adjusting therapy based on the monitored PEI.

15. The implantable system of claim 13, further comprising memory, wherein the PEI monitor is also configured to store, within memory, information indicative of the monitored PEI so that the stored information is available for transfer to a non-implanted system.

16. The implantable system of claim 13, wherein the PEI monitor is configured to monitor changes in the patient's PEI by monitoring changes in the interval over time.

17. The implantable system of claim 13, wherein the predetermined feature indicative of cardiac electrical activity is selected from the group consisting of:
- a Q-wave;
- a R-wave; and
- a QRS complex.

18. The implantable system of claim 13, wherein the predetermined feature indicative of changes in arterial blood volume is selected from the group consisting of:
- a foot of the signal indicative of changes in arterial blood volume;
- a peak of the signal indicative of changes in arterial blood volume; and
- a maximum positive slope of the signal indicative of changes in arterial blood volume.

19. The implantable system of claim 13, wherein the PEI monitor is further configured to factor the transit time out of the interval when monitoring the patient's PEI.

20. For use with an implantable system, a method for monitoring a patient's pre-ejection interval (PEI), the method comprising:
- (a) obtaining an ABV signal indicative of changes in arterial blood volume (ABV) at a sensor;
- (b) determining a transit time representing at least one of i) a delay from an onset of cardiac electrical activity (CEA) to when the ABV signal arrives at the sensor or ii) a time for a pressure pulse to travel from an aorta to the implanted sensor; and
- (c) monitoring the patient's PEI based on the ABV signal indicative of changes in arterial blood volume and the transit time.

* * * * *